US011020486B2

(12) United States Patent
Beaurline et al.

(10) Patent No.: US 11,020,486 B2
(45) Date of Patent: Jun. 1, 2021

(54) SESAME OIL BASED INJECTION FORMULATIONS

(71) Applicant: 3M Innovative Properties Company, St. Paul, MN (US)

(72) Inventors: Joseph M. Beaurline, St. Paul, MN (US); James M. Elvecrog, St. Paul, MN (US); John P. Vasilakos, St. Paul, MN (US); John Thomas Capecchi, St. Paul, MN (US); Karen Elizabeth Johnson, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 485 days.

(21) Appl. No.: 15/032,773

(22) PCT Filed: Oct. 30, 2014

(86) PCT No.: PCT/US2014/063095
§ 371 (c)(1),
(2) Date: Apr. 28, 2016

(87) PCT Pub. No.: WO2015/069535
PCT Pub. Date: May 14, 2015

(65) Prior Publication Data
US 2016/0271259 A1    Sep. 22, 2016

Related U.S. Application Data

(60) Provisional application No. 61/900,255, filed on Nov. 5, 2013.

(51) Int. Cl.
| A61K 47/44 | (2017.01) |
| A61K 9/00 | (2006.01) |
| C07D 471/04 | (2006.01) |
| A61K 31/4745 | (2006.01) |
| A61K 47/10 | (2017.01) |

(52) U.S. Cl.
CPC ............ *A61K 47/44* (2013.01); *A61K 9/0019* (2013.01); *A61K 31/4745* (2013.01); *A61K 47/10* (2013.01); *C07D 471/04* (2013.01)

(58) Field of Classification Search
CPC .................................................. A61K 31/4745
See application file for complete search history.

(56) References Cited

U.S. PATENT DOCUMENTS

| 4,689,339 A | 8/1987 | Karjalainen et al. |
| 4,863,970 A | 9/1989 | Patel et al. |
| 4,929,624 A | 5/1990 | Gerster et al. |
| 5,266,575 A | 11/1993 | Gerster et al. |
| 5,268,376 A | 12/1993 | Gerster |
| 5,346,905 A | 9/1994 | Gester |
| 5,352,784 A | 10/1994 | Nikolaides et al. |
| 5,389,640 A | 2/1995 | Gerster et al. |
| 5,446,153 A | 8/1995 | Lindstrom et al. |
| 5,482,936 A | 1/1996 | Lindstrom |
| 5,756,747 A | 5/1998 | Gerster |
| 6,110,929 A | 8/2000 | Gerster et al. |
| 6,194,425 B1 | 2/2001 | Gerster et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,573,273 B1 | 6/2003 | Crooks et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,756,382 B2 | 6/2004 | Coleman et al. |
| 7,799,800 B2 | 9/2010 | Wightman |
| 8,138,311 B2 | 3/2012 | Rosenblum et al. |
| 8,239,070 B1 | 8/2012 | Schlueter et al. |

(Continued)

FOREIGN PATENT DOCUMENTS

| EP | 1 653 959 B1 | 5/2015 |
| JP | H0262483 A | 3/1990 |

(Continued)

OTHER PUBLICATIONS

Strickley, R. G. Pharmaceutical Research, vol. 21, No. 2, Feb. 2004, 201-230. (Year: 2004).*
Formulation and Routes of Administration of Drugs. Pharmacology I Mar. 28, 2011,10 pages. (Year: 2011).*
Banker et al., Ed. "Parenteral products: Nonaqueous and Mixed Vehicles" from Modern Pharmaceutics: Fourth Edition. CRC Press: Florida, p. 593. (Year: 2002).*
Al-Achi et al. "17.2 Formulation Design: 17.2.2.1.4 Oil Solubilization and Stabilization" from "Integrated Pharmaceutics Applied Preformulation, Product Design, and Regulatory Science". Wiley: New Jersey, p. 477 (Year: 2013).*
(U1) Kikugawa et al. "Butylated Hydroxyanisole (BHA)" from "Food Antioxidants". B.J.F Hudson, Ed. Elsevier: New York. pp. 68-69. (Year: 1990).*

(Continued)

*Primary Examiner* — Amy L Clark
(74) *Attorney, Agent, or Firm* — Eric E. Silverman

(57) ABSTRACT

Injectable formulations comprising ethanol, sesame oil, and an Immune Response Modifier compound are disclosed. Methods of making the formulations and methods of using the formulations for treatment of a disease in a subject, e.g., neoplastic disease, comprising injecting the formulations into a subject hi need of treatment, are also provided.

11 Claims, No Drawings

(56) References Cited

U.S. PATENT DOCUMENTS

| | | |
|---|---|---|
| 9,678,976 B2 | 6/2017 | Lambright |
| 10,406,142 B2 | 9/2019 | Wightman |
| 2003/0139364 A1 | 7/2003 | Krieg et al. |
| 2003/0199538 A1* | 10/2003 | Skwierczynski .... A61K 9/0014 514/291 |
| 2004/0141950 A1 | 7/2004 | Noelle et al. |
| 2004/0265351 A1 | 12/2004 | Miller et al. |
| 2007/0123558 A1 | 5/2007 | Statham et al. |
| 2009/0035323 A1 | 2/2009 | Stoermer et al. |
| 2011/0021554 A1 | 1/2011 | Stoesz et al. |
| 2013/0230578 A1 | 9/2013 | Wightman |

FOREIGN PATENT DOCUMENTS

| | | | |
|---|---|---|---|
| WO | WO 2005/001022 | 1/2005 | |
| WO | WO 2011/112669 | 9/2011 | |
| WO | WO 2011/112669 A1 | 9/2011 | |
| WO | WO-2012024284 A1 * | 2/2012 | ........... A61K 9/0019 |

OTHER PUBLICATIONS (V1) Heller, Jr. Journal of the National Cancer Institute. vol. 19, No. 5. p. 978 (1 page). (Year: 1957).*

(W1) Seibert, A. "Hypodermic Injections of Salicylates in Rheumatism" from Medical Record: A weekly Journal of Medicine and Surgery. Stedman, TL, ed. vol. 79. William Wood and Company. 1911. 1 page. (Year: 1911).*

(X1) Tokusoglu, et al. GRASAS Y ACEITES, 60 (2), Apr.-Jun. 2009, 119-124. (Year: 2009).*

International Search Report for International Application No. PCT/US14/63095; dated Feb. 24, 2015.

Written Opinion for International Application No. PCT/US14/63095; dated Feb. 24, 2015.

Zhang et al., "Pharmaceutics," Peking University Medical Press, the 1st edition, Jan. 2005, pp. 99-100.

Belikov, Farmacevticheskaya himiya, M., Vysshaya shkola, 1993, pp. 43-47.

Dilantin®, "NDA 010151 Dilantin injection S-038," Federal Drug Administration [online], [retrieved from the internet on Jan. 27, 2020], <https://www.accessdata.fda.gov/drugsatfda_docs/label/2014/008762s050,010151s038lbl.pdf> 32 pages.

"Diazepam Injection, USP," Dailymed [online], [retrieved from the internet on Jan. 27, 2020], <https://dailymed.nlm.nih.gov/dailymed/fda/fdaDrugXsl.cfm?setid=0fb9bdfb-4d92-483e-acfe-4c9b2a84441c&type=display> 10 pages.

Raymond et al. "Handbook of Pharmaceutical Excipients," 2006, *Pharmaceutical Press*, p. 646.

Reproductive Biology and Endocrinology, May 18, 2009, 7(47):1-11.

Revised Pharmaceutical Additive Handbook, Feb. 28, 2007, pp. 330-332.

Singh et al. 2014, *J. Mimmunol*, 193(9): 4722-33.

Tashiro et al., Oil and minor components of sesame (*Sesamum indicum* L.) strains, 1990, *Journal of the American Oil Chemists' Society*, 67:508-11.

Vaccine, 29, 2011, 5434-5442, XP028240658.

* cited by examiner

SESAME OIL BASED INJECTION FORMULATIONS

This application is a 35 U.S C. § 371 national stage filing of International Application No. PCT/US2014/06309.5, filed Oct. 30, 2014, and claims priority under 35 § 1 19(e) to U.S. provisional application Ser. No. 61/900,255, filed Nov. 5, 2013, entitled "Sesame Oil Based Injection Formulations", the contents of which are hereby incorporated by reference.

CROSS-REFERENCE TO RELATED APPLICATIONS

This application claims priority to U.S. provisional patent application Ser. No. 61/900,255, filed Nov. 5, 2013, the entire disclosure of which is incorporated herein by reference.

BACKGROUND

There have been important advances in recent years regarding understanding of the immune system and discovery of drug compounds for modifying immune response to treat or prevent disease. Such immune response modifier ("IRM") compounds have been discovered in a variety of compound classes, including imidazoquinoline amines, imidazopyridine amines, 6,7-fused cycloalkylimidazopyridine amines, 1,2-bridged imidamquinoline amines, thiazoloquinoline amines, oxazoloquinoline amines, thiazolopyridine amines, oxazolopyridine amines, imidazonaphthyridine amines, imidazotetrahydronaphthyridine amines, and thiazolonaphthyridine amines. See, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,477,347; 6,677,348; 6,677,349; 6,683,088; 6,756,382; 7,799,800; U.S. Patent Publication Nos. 2012/040461 and 2013/0230578. Many of these compounds have demonstrated potent immunostimulating, antiviral and antitumor (including anticancer) activity, and have also been shown to be useful as vaccine adjuvants and treatment of TH2-mediated diseases.

However, the ability to provide desired therapeutic benefits of such compounds depends on a variety of factors, including the extent to which they can be formulated and delivered in a way that is suitable for particular treatments. Accordingly, there is a need for new methods and formulations to provide the potential therapeutic benefits from these important immunomodifying drug compounds.

SUMMARY

While many diseases may be treated by systemic delivery of immune response modifying compounds, systemic delivery can have increased negative side effects, such as systemic TNF induction, as compared to localized delivery, and can also limit the amount of IRM compound therapeutically available to treat the disease by spreading it throughout the body. While some advancements have been made in localized delivery of IRMs (see, e.g., U.S. Pat. No. 7,799,800 and U.S. Patent Publication Nos. 2004/0265351; 2009/0035323; and 2013/0230578), there remains a need for stable formulations that provide increased localization of IRM delivery.

It has been found that formulations comprising an IRM compound, ethanol, and sesame oil provide locally active IRM compounds for an extended period of time.

The present invention provides injectable formulations comprising ethanol, sesame oil, and an Immune Response Modifier (IRM) compound. The IRM compound generally has the formula (I):

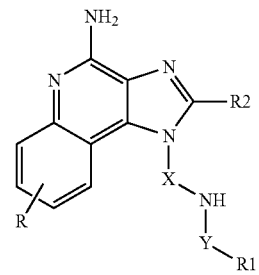

wherein R, $R_2$, X, Y, and $R_1$ are as defined below.

In another aspect, the invention provides a method of delivering the pharmaceutical formulations described herein, comprising injecting the formulation into a subject.

In another aspect, the invention provides a method of treating a disease, comprising injecting into a subject in need of treatment of the disease any one of the formulations described herein.

In another aspect, the present invention further provides a method of making pharmaceutical formulations comprising ethanol, sesame oil, and an IRM compound of Formula I.

The terms "comprises" and variations thereof do not have a limiting meaning where these terms appear in the description and claims.

As used herein, "a", "an", "the", "at least one", and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

"Induce" and variations thereof refer to any measurable increase in cellular activity. For example, induction of an immune response may include, for example, an increase in the production of a cytokine, activation, proliferation, or maturation of a population of immune cells, and/or other indicator of increased immune function.

"Therapeutic" and variations thereof refer to a treatment that ameliorates one or more existing symptoms or clinical signs associated with a condition.

"Treat" or variations thereof refer to reducing, limiting progression, ameliorating, preventing, or resolving, to any extent, the symptoms or signs related to a condition.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION

The present invention is directed to methods and formulations of immune response modifiers (IRMs) that can be deposited, in some embodiments via injection, within a localized tissue region and can provide locally active IRM compounds for an extended period of time. The formulations described herein exhibit a high degree of stability, particularly of the IRM compound.

In general, the formulations of the present invention comprise ethanol, sesame oil, and an IRM compound having, the following formula (I):

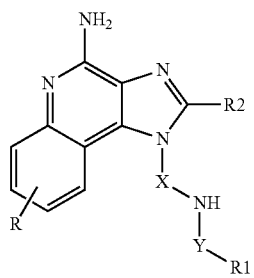

I wherein:

X is alkylene having up to 8 carbon atoms optionally interrupted or terminated by —O—;

$R_2$ is hydrogen, alkyl, alkoxyalkylenyl, alkylaminoalkylenyl, or hydroxyalkylenyl;

Y is —C(O)— or —S(O)$_2$—;

$R_1$ is a linear or branched aliphatic group having 11-23 carbon atoms, optionally including one or more unsaturated carbon-carbon bonds: and R is hydrogen, halogen, or hydroxyl, or a pharmaceutically acceptable salt thereof.

As used herein, the terms "alkyl", "alkenyl", and the prefix "alk-" are inclusive of both straight chain and branched chain groups and of cyclic groups, e.g. cycloalkyl and cycloalkenyl. Unless otherwise specified, these groups contain from 1 to 23 carbon atoms, with alkenyl groups containing from 2 to 23 carbon atoms. In some embodiments, these groups have a total of up to 20 carbon atoms, up to 18 carbon atoms, up to 16 carbon atoms, up to 10 carbon atoms, up to carbon atoms, up to 7 carbon atoms, up to 6 carbon atoms, or up to 4 carbon atoms. Cyclic groups can be monocycle or polycyclic and preferably have from 3 to 10 ring carbon atoms. Exemplary cyclic groups include cyclopropyl, cyclopropylmethyl cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an alkoxyakylenyl group comprises in alkylene moiety to which an alkoxy group is attached.

An alkylene group with carbon atoms optionally "interrupted" by —O— refers to having carbon atoms on either side of the —O—. An example is —CH$_2$—CH$_2$—O—CH$_2$—CH$_2$—.

An alkylene group with carbon atoms optionally "terminated" by —O— refers to having the —O— on either end of the alkylene group or chain of carbon atoms. Examples include —O—CH$_2$—CH$_2$—CH$_2$—CH$_2$— and —CH$_2$—CH$_2$—CH$_2$—CH$_2$—O—. In the compounds used in the present invention, when X is alkylene having up to 8 carbon atoms terminated by —O—, the —O— may be connected to either the nitrogen of the imidazole ring or the nitrogen of the amide (Y is —C(O)—) or sulfonamide (Y is —S(O)2—) group.

The invention is inclusive of the IRM compounds described herein (including intermediates) in any of their pharmaceutically acceptable forms, including solid, semisolid, solvates (e.g., hydrate), isomers (e.g., diastereomers and enantiomers), salts, polymorphs, prodrugs, and the like. In particular, if a compound is optically active, the invention specifically includes each of the compound's enantiomers as well as racemic mixtures of the enantiomers it should be understood that the term "compound" includes any or all of such forms, whether explicitly stated or not (although at times, "salts" are explicitly stated).

For any of the compounds presented herein, including Formula I, each one of the following variables (e.g., X, $R_2$, R, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

In some embodiments, X is alkylene having up to 8 carbon atoms optionally interrupted or terminated by —O—.

In some embodiments, X is alkylene having up to 4 carbon atoms optionally interrupted by or terminated by —O—.

In some embodiments, X is —O—C$_{2-8}$ alkylene (e.g., —O—C$_{2-5}$ alkylene). In these embodiments, the —O— is directly attached to the nitrogen of the imidazole ring.

In some embodiments, X is —O—C$_{3-8}$alkylene (e.g., —O—C$_{3-5}$ alkylene). In these embodiments, the —O— is directly attached to the nitrogen of the imidazole ring.

In some embodiments, X is —C$_{1-8}$ alkylene alkylene), —C$_{2-5}$ alkylene).

In some embodiments, X is —C$_{2-8}$ alkylene —C$_{2-5}$ alkylene) that is interrupted by —O—.

In some embodiments, X is —C$_{3-8}$ alkylene (e.g., —C$_{3-5}$ alkylene).

In some embodiments, X is —O—butylene (e.g., —O—CH$_2$—CH$_2$—CH$_2$—CH$_2$—). In these embodiments, the —O— is directly attached to the nitrogen of the imidazole ring.

In some embodiments, X is —CH$_2$—CH$_2$—O—CH$_2$—CH$_2$—.

In some embodiments, including any of the above embodiments of Formula I, where X is defined, $R_2$is hydrogen, alkyl, alkoxyalkylenyl, alkylaminoalkylenyl, or hydroxyalkylenyl.

In some embodiments, including any of the above embodiments of Formula I, where X is defined, $R_2$ is hydrogen, alkyl, alkoxyalkylenyl, or hydroxyalkylenyl.

In some embodiments, including any of the above embodiments of Formula I, where X is defined, $R_2$ is hydrogen, alkyl, or alkoxyalkylenyl.

In some embodiments, including any of the above embodiments of Formula I, where X is defined, $R_2$ is methyl, ethyl, propyl, butyl, ethoxymethyl, methoxymethyl, ethylaminomethyl, or 2-methoxyethyl.

In some embodiments, including any of the above embodiments of Formula I, where X is defined, $R_2$ is methyl, ethyl, propyl, butyl, ethoxymethyl, methoxymethyl, or 2-methoxyethyl.

In some embodiments, including any of the above embodiments of Formula I, where X is defined, $R_2$ is ethyl, butyl, ethoxymethyl, or 2-methoxyethyl.

In some embodiments, including any of the above embodiments of Formula I, where X is defined, $R_2$ is $C_{1-4}$ alkyl.

In some embodiments, including any of the above embodiments of Formula I, where X is defined, $R_2$ is butyl (e.g., —$CH_2$—$CH_2$—$CH_2$—$CH_3$).

In some embodiments, including any of the above embodiments of Formula I, where X is defined, $R_2$ is ethoxymethyl (e.g., —$CH_2$—O—$CH_2$—$CH_3$).

In some embodiments, including any of the above embodiments of Formula I where X is defined, $R_2$ is 2-methoxyethyl (e.g., —$CH_2CH_2$—O—$CH_3$).

In some embodiments, including any of the above embodiments of Formula I, where X is defined, $R_2$ is ethylaminomethyl —$CH_2$—NH—$CH_2$—$CH_3$).

In some embodiments, including any of the above embodiments of Formula I, where X or $R_2$ is defined, R is hydrogen, halogen, hydroxyl, alkyl, haloalkyl, or alkoxy.

In some embodiments, including any of the above embodiments of Formula I, where X or $R_2$ is defined, R is halogen or hydroxyl.

In some embodiments, including any of the above embodiments of Formula I, where X or $R_2$ is defined, R is hydrogen.

In some embodiments, including any of the above embodiments of Formula I, where X or $R_2$ is defined, R is halogen. In some embodiments, R is fluorine, chlorine, or bromine.

In some embodiments, including any of the above embodiments of Formula I, where X, R, or $R_2$ is defined, Y is —C(O)— or —S(O)$_2$—.

In some embodiments, including any of the above embodiments of Formula I, where X, R, or $R_2$ is defined, Y is —C(O)—.

In some embodiments, including any of the above embodiments of Formula I, where X, R, $R_2$, or Y is defined, $R_1$ is a linear or branched aliphatic group having 11-23 carbon atoms, optionally including one or more unsaturated carbon-carbon bonds (e.g., —$(CH_2)_7$—CH=CH—$(CH_2)_7$—$CH_3$, —$(CH_2)_7$—CH=CH—$(CH_2)_5$—$CH_3$, —$(CH_2)_9$—CH=CH—$(CH_2)_5$—$CH_3$, —$(CH_2)_6$—$(CH_2$—CH=CH)$_2$—$(CH_2)_4$—$CH_3$, —$(CH_2)_6$—$(CH_2$—CH=CH)$_3$—$CH_2$—$CH_3$, or —$(CH_2)_2$—$(CH_2$—CH=CH)$_4$—$(CH_2)_4$—$CH_3$).

In some embodiments, including any of the above embodiments of Formula I, where X, R, $R_2$, or Y is defined, $R_1$ is $C_{11}$-$C_{23}$ alkyl.

In some embodiments, including any of the above embodiments of Formula I, where X, R, $R_2$, or Y is defined, $R_1$ is $C_{15}$-$C_{23}$ alkyl.

In some embodiments, including any of the above embodiments of Formula I, where X, R, $R_2$, or Y is defined, $R_1$ is $C_{15}$-$C_{19}$ alkyl.

In some embodiments, including any of the above embodiments of Formula I, where X, R, $R_2$, or Y is defined, $R_1$ is $C_{15}$-$C_{17}$ alkyl.

In some embodiments, including any of the above embodiments of Formula I, where X, R, $R_2$, or Y is defined, $R_1$ is $C_{17}$ alkyl.

In some embodiments of Formula I, X is —O—$C_{3-5}$alkylene, and is methyl, ethyl, propyl, butyl, ethoxymethyl, methoxymethyl, or 2-methoxyethyl.

In some embodiments of Formula I, X is —O-butylene, and $R_2$ is butyl.

In some embodiments of Formula I, X is —O-butylene, a straight chain or branched chain alkyl group.

In some embodiments of Formula I, $R_1$ is a straight chain alkyl group.

In some embodiments, the compound of Formula I is N-(4-{[4-amino-2-butyl-1H-imidazo[4,5-c]quinolin-1-yl]oxy}butyl)octadecanamide:

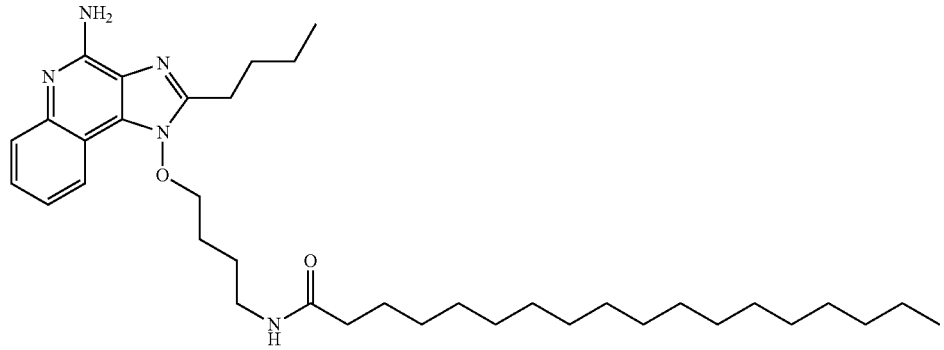 [SMILES: CCCCCCCCCCCCCCCCCC(=O)NCCCCOn1c(CCCC)nc2c(N)nc3ccccc3c21]

or a pharmaceutically acceptable salt thereof.

IRM compounds used the formulations of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, N.Y., (1967-1999 ed.); Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der organischen Chemie, 4, Aufl. Ed. Springer-Verlag, Berlin, Germany, including supplements (also available via the Beilstein online database)).

For more detailed description of the individual reaction steps useful for preparing compounds of Formula I, see, e.g., U.S. Pat. No 7,799,800; and U.S. Patent. Publication No. 2013/0230578.

The compounds of Formula I can also be prepared from advanced intermediate compounds described in the prior art. The compounds of Formula I can be prepared from the advanced intermediate compounds of formula XIV, XXIV, and XXXVI that are described in Reaction Schemes II, III, and IV respectively of International Patent Application No. WO2012/167081. The compounds of Formula I can also be prepared from the advanced intermediate compound of formula VII in Reaction Scheme I or from the advanced intermediate compound of formula VIII in Reaction Scheme II that are both described in U.S. Pat. No. 6,451,810. Synthetic procedures to prepare the above advanced intermediate compounds are also described in International Patent Application No WO2012/167081 and U.S. Pat. No. 6,451,810.

The compounds of Formula I where X is —C(O)— can be prepared by reacting the above advanced intermediate compounds with the appropriate carboxylic acid or carboxylic acid chloride compound using the procedures described in Reaction Schemes II-III of U.S. Pat. No. 6,451,810. Preferred Formula I compounds where X is —C(O)— can be prepared using the following carboxylic acids (or the corresponding carboxylic acid chloride derivatives); lauric acid, myristic acid palmitic acid, margaric acid, stearic acid, arachidic acid, behenic acid, and lignoceric acid. Formula I compounds where X is —C(O)— and R1 is an unsaturated aliphatic group (i.e. an aliphatic group having one or more unsaturated carbon-carbon bonds) can be prepared from unsaturated fatty acids such as oleic acid, palmitoleic acid, vaccenic acid, linoleic acid, linoleneic acid, or arachidonic acid.

The compounds of Formula I where X is —S(O)$_2$— can be prepared by reacting the above advanced intermediate compounds with the appropriate sulfonyl chloride using the procedures described in Reaction Scheme II of U.S. Pat. No. 6,331,539.

Those skilled in the art will appreciate that other synthetic routes may be used to synthesize the compounds of the invention.

In the preparation of the IRM compounds used in the formulations of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic. Synthesis*, John Wiley & Sons, New York, USA, 1991.

Conventional methods and techniques of separation and purification can be used to isolate the IRM compounds used in the formulations of the invention. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

The ethanol used in the injectable formulations described herein is typically present in an amount of from about 1 wt-% to about 9 wt-%. in some embodiments, the ethanol is present in an amount from about 3 wt-% to about 8 wt-%. In some embodiments the ethanol is present in an amount from about 5 wt-% to about 7.5 wt-%. In some embodiments, the ethanol is present in an amount from about 1 wt-% to about 3 wt-%. In some embodiments, the ethanol is present in an amount from about 3 wt-% to about 4 wt-%. In some embodiments, the ethanol is present in an amount from about 4 wt-% to about 5 wt-%. in some embodiments, the ethanol is present in an amount from about 5 wt-% to about 6 wt-%. In some embodiments, the ethanol is present in an amount from about 6 wt-% to about 7 wt-%. In some embodiments, the ethanol is present in an amount from about 6.5 wt-% to about 7.5 wt-%. In some embodiments, the ethanol is present in an amount from about 8 wt-% to about 9 wt-%. In some embodiments, as described in the methods below, an excess of ethanol (i.e. greater amount than is soltible in sesame oil), e.g., in some embodiments at least 10 wt-% ethanol, in some embodiments at least 12 wt-% ethanol, in some embodiments at least 14 wt-% ethanol, is used to dissolve greater amounts of IRM compound. When the IRM-ethanol solution is added to the sesame oil, the IRM dissolves much more quickly than simply adding the IRM to a premixed sesame oil-ethanol solution; the excess ethanol (that is present beyond the solubility limits in sesame oil) is then evaporated off to produce the final formulation (containing 9 wt-% ethanol or less). In some embodiments, ethanol suitable for use in the injectable formulations described herein include ethanol that does not contain any water or denaturant. Exemplary ethanol useful in the formulations of the present invention includes 200 proof ethanol, e.g., Dehydrated Alcohol, USP grade.

The injectable formulations described herein also include sesame oil. The sesame oil used in the formulations described herein is pharmaceutical grade, such as Sesame Oil, NF. In some embodiments, the sesame oil may be refined such that one or more polar compounds have been substantially removed from the sesame oil or reduced in content without substantially altering the fatty acid profile of the sesame oil. For example, the sesame oil may have a fatty acid profile that includes palmitic acid, stearic acid, oleic acid, and linoleic acid. Other fatty acids may also be present at lower levels, typically less than 1 wt-%. Polar compounds present in sesame oil can include but are not limited to compounds such as monoglycerides, diglycerides, free fatty acids, plant sterols, coloring matter (chlorophyll, carotene), sesamin, sesamolin, products resulting from oxidation, and environmental chemicals. Polar compounds in sesame oil can be quantitatively measured using standard tests such as the acid value test, hydroxyl value test, peroxide value test, and trace nitrogen value test. Standard chromatography methods can be used to remove or substantially reduce the content of at least one polar compound from sesame oil to provide a refined sesame oil. Suitable chromatographic methods that are well known in the art include gravity based column chromatography, flash column chromatography, medium pressure liquid chromatography, or high pressure chromatography.

In some embodiments, the sesame oil has a hydroxyl value less than or equal to 2. The hydroxyl value of sesame oil can be determined according to the published procedure described in USP 36 <401> Fats and Fixed Oils, Hydroxyl Value. In some embodiments, the acid value of the sesame oil is less than or equal to 0.1. The acid value of sesame oil can be determined according to the published procedure described in USP 36 <401>Fats and Fixed Oils, Acid Value. In some embodiments, the peroxide value of the sesame oil is less than or equal to 1. The peroxide value of sesame oil can be determined according to the published procedure described in USP 36 <401> Fats and Fixed Oils, Peroxide Value. In some embodiments, the total nitrogen content of the sesame oil is less than or equal to 1 ppm. The trace nitrogen value of sesame oil can be determined according to the published method described in ASTM D5762-12. In some embodiments, the sesame oil contains contains no more than 0.05 wt-% of sesamin. In some embodiments, the sesame oil contains no more than 0.05 wt-% of sesamolin. The levels of sesamin and sesamolin can be determined according to the published sesamin/sesamolin assay described by T. Tashiro, Y. Fukuda. T. Osawa and M. Namiki in *Journal of the American Oil Chemists' Society*, 67, 508 (1990).

It has surprisingly been found that formulations comprising an IRM compound, ethanol, and refined sesame oil, as described above such that one or more polar compounds have been substantially removed from the sesame oil, have increased stability, not only of the formulation in general, but also of the IRM compound itself. The formulations described herein exhibit a high degree of chemical and physical stability, particularly of the IRM compound. For example, in some embodiments described herein, such as where refined sesame oil is used, the formulations exhibit an acceptable shelf life for commercial use, e.g., 6-month shelf life. 1-year shelf life, and the like.

In some embodiments, an injectable pharmaceutical formulation of the present invention comprises sesame oil, ethanol (7.5 wt-%), BHA (300 ppm), and N-(4-{[4-amino-2-butyl-1H-imidazo[4,5-c]quinolin-1-yl]oxy}butyl)octadecanamide (0.15 mg/mL). In some embodiments, an injectable pharmaceutical formulation of the present invention comprises sesame oil, ethanol (7.5 wt-%), BHA (300 ppm), and N-(4-{[4-amino-2-butyl-1H-imidazo[4,5-c]quinolin-1-yl]oxy}butyl)octadecanamide (0.3 mg/mL). In some embodiments, an injectable pharmaceutical formulation of the present invention comprises sesame oil, ethanol (7.5 wt-%), BHA (300 ppm), and N-(4-{[4-amino-2-butyl-1H-imidazo[4,5-c]quinolin-1-yl]oxy}butyl)octadecanamide (0.6 mg/mL). In some embodiments, an injectable pharmaceutical formulation of the present invention comprises sesame oil, ethanol (7.5 wt-%), BHA (300 ppm), and N-(4-{[4-amino-2-butyl-1H-imidazol[4,5-c]quinolin-1-yl]oxy}butyl)octadecanamide (1.2 mg/mL). In some embodiments, an injectable pharmaceutical formulation of the present invention comprises sesame oil, ethanol (7.5 wt-%, BHA (300 ppm), and N-(4-{[4-amino-2-butyl-1H-imidazo[4,5-c]quinolin-1-yl]oxy}butyl)octadecanamide (2.4 mg/mL).

In some embodiments, an injectable pharmaceutical formulation of the present invention comprises sesame oil, ethanol (7.5 wt-%), BHA (300 ppm), and N-(4-{[4-amino-2-butyl-1H-imidazo[4,5-c]quinolin-1-yl]oxy}butyl)octadecanamide (from 0.1 to about 2.5 mg/mL).

Factors involved in the selection of an injectable formulation include solubility of the IRM compound in the formulation, stability of the IRM compound in the formulation, physical stability of the formulation. These factors are especially important when designing a formulation that can be stored for long periods of time (>6 months) and at temperatures ranging from 5° C. to 40° C.

The chemical stability of the IRM compound in the formulation can be influenced by the chemical composition of the formulation and the storage conditions. The chemical stability of the IRM compound in the formulation can be determined by analyzing for the IRM compound content in the formulation over time using standard analytical methods such as HPLC.

In some embodiments, the pharmaceutical formulations may further include one or more additives including, but not limited, to, antioxidants, antimicrobials, adjuvants, thickeners, suspending agents, surfactants, and dispersing agents. In some embodiments the formulation can include an added antioxidant such as butylated hydroxyanisole (BHA) or butylatedhydroxytoluene (BHT). The added antioxidant concentration in the formulation can be at least 10 ppm, 50 ppm, 100 ppm, 200 ppm, and up to 300 ppm.

In some embodiments, the pharmaceutical formulations and methods of the present disclosure can include other additional active agents, e.g., in admixture or administered separately. Such additional agents can include an antigen (e.g., a vaccine), a chemotherapeutic agent, a cytotoxic agent, an antibody, an antiviral agent, a cytokine, a tumor necrosis factor receptor (TNFR) agonist, or an additional immune response modifier, TNFR agonists that may be delivered in conjunction with a formulation of the present invention include CD40 receptor agonists, such as disclosed in application U.S. Pat. Appl. Pub. No. 2004/0141950 (Noelle et al.). Other active ingredients for use in combination with an IRM formulation of the present invention include those disclosed in, e.g., U.S. Pat. Appl. Pub. No. 2003/0139364 (Krieg et al.).

IRM compounds of Formula I have been shown to induce production of cytokines such as TNF-α (see. e.g., U.S. Pat. No. 7,799,800; and U.S. Patent Publication No, 2013/0230578). The ability to induce cytokine production indicates that the IRM compounds used in formulations of the invention can modulate the immune response in a number of different ways, rendering the IRM compounds useful in the treatment of a variety of disorders. Other cytokines whose production may be induced by the administration of the formulations disclosed herein generally include Type I interferons (e.g., INF-α), IL-1, IL-6, IL-8, IL-10, IL-12, MIP-1, MCP-1, and a variety of other cytokines. Among other effects, these and other cytokines inhibit virus production and tumor cell growth, making the formulations of the present invention useful in the treatment of viral diseases and neoplastic diseases. For example, tumor necrosis factor, interferons, or interleukins have been shown to stimulate a rapid release of certain monocyte/macrophage-derived cytokines and are also capable of stimulating B cells to secrete antibodies which play an important role in antiviral and antitumor activities.

In some embodiments, formulations of the present invention are useful for the treatment of solid tumors such as head and neck tumors, breast tumors, lymphoma, melanoma, and bladder tumors. In some embodiments, formulations of the present invention are useful for the treatment of cutaneous T cell lymphoma.

In some embodiments, formulations of the present invention are useful for the treatment of viral warts and hypertrophic, or keloid, scars.

The present invention further provides a method of delivering the pharmaceutical formulations described herein, comprising injecting the formulation into a subject. The injection may be, e.g., subcutaneous, intramuscular, or into a selected tissue site, such as a tumor mass. In some embodiments, the formulation is injected into a tumor mass, a wart, or hypertrophic scar tissue.

The present invention further provides a method of treating a disease, comprising injecting into a subject in need of treatment of the disease the any one of the formulations described herein.

The methods of the present invention may be performed on any suitable subject. Suitable subjects include animals such as humans, non-human primates, rodents, dogs, cats, horses, pigs, sheep, goats, or cows.

The animal to which the formulation is administered for treatment may have a disease (e.g., a viral or neoplastic disease), and administration of the compound may provide therapeutic treatment. Exemplary conditions that may be treated by administering a formulation of the present invention include:

(a) neoplastic diseases such as melanoma, leukemias (e.g., myelogenous leukemia, chronic lymphocytic leukemia, multiple myeloma, non-Hodgkin's lymphoma, cutaneous T-cell lymphoma, B-cell lymphoma, and hairy cell leukemia), breast cancer, lung cancer, prostate cancer, colon cancer, head or neck cancers, bladder cancer, and other cancers;

(b) viral diseases such as diseases resulting from infection by a poxvirus (e.g., an orthopoxvirus such as variola or vaccinia, or molluscum contagiosum), or a papovavirus (e.g., papillomaviruses, such as those that cause genital warts, common warts, or plantar warts);

(c) diseases associated with wound repair such as inhibition of keloid formation and other types of scarring (e.g., enhancing wound healing, including chronic wounds).

In some embodiments, the disease treated is a neoplastic disease. In some embodiments, the formulation is injected into a tumor mass. In some embodiments, the disease treated is selected from a head or neck cancer, breast cancer, lymphoma, melanoma, and bladder cancer.

In some embodiments, the disease treated is a viral disease that causes warts. In some embodiments, the formulation is injected into a wart.

It will be understood that in the treatment of the diseases mentioned above, for example, the formulations disclosed herein can also be used in combination with other therapies such as other active agents and other procedures (e.g., radiation, chemotherapy, chemoablation, laser ablation, cryotherapy, and surgical excision).

The precise amount of a IRM compound in the formulations that will be therapeutically effective for methods according, to the present invention, and the dosing regimen, for example, will vary according to factors known in the art including the nature of the carrier, the size and state of the subject's immune system (e.g., suppressed, compromised, stimulated), the species to which the formulation is being administered, the dosing regimen selected, the application site, the particular formulation, and the condition being treated. Accordingly, it is not practical to set forth generally the composition of a formulation that includes ethanol, sesame oil, and an IRM compound of Formula I or an amount of the IRM compound that constitutes an effective amount, or a dosing regimen that is effective for all possible applications. Those of ordinary skill in the art, however, can readily determine appropriate formulations, therapeutically effective amounts of the IRM compound, and dosing regimen based on the guidance provided herein, information available in the art pertaining to IRM compounds, and routine testing. The term "a therapeutically effective amount" thus means an amount of the IRM compound sufficient to induce a therapeutic or prophylactic effect, such as cytokine induction, inhibition of TH2 immune response, antiviral or antitumor activity, reduction of scarring, or enhanced wound healing.

An amount of a formulation or IRM compound in the formulation effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over a background level of such cytokines. The precise amount will vary according to factors known in the art but is expected to be a dose of about 100 nanograms per kilograms (µg/kg) to about 50 milligrams per kilogram (mg/kg), in some embodiments about 10 micrograms per kilogram (µg/kg) to about 5 mg/kg, about 100 µg/kg to about 1 mg/kg, or about 0.01 mg/m$^2$ to about 10 mg/m$^2$. Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184. An amount effective to treat or inhibit a viral infection, for example, is an amount that will cause a reduction in one or more of the manifestations of viral infection, such as viral lesions, viral load, rate of virus production, and mortality as compared to untreated control animals and may include any of the aforementioned doses. An amount of a compound or pharmaceutical composition effective to treat a neoplastic condition is an amount that will cause a reduction in tumor size or in the number of tumor foci and may include any of the aforementioned doses.

Formulations of the invention may induce the production of certain cytokines and are useful as immune response modifiers that can modulate the immune response in a number of different ways, rendering them useful in the treatment of a variety of disorders. Among other effects, these and other cytokines can inhibit virus production and tumor cell growth, making the formulations useful for, e.g., treatment of viral and neoplastic diseases. It should also be noted that the formulations may be administered prior to acquiring a disease so that administration of the formulation may provide a prophylactic treatment.

In addition to the ability to give rise to cytokine induction, formulations of the invention may bring about an effect on other aspects of the innate immune response. For example, natural killer cell activity may be stimulated, an effect that may be due to cytokine induction. The formulations may also bring about activation of macrophages, which in turn stimulate secretion of nitric oxide and the production of additional cytokines. Further, the formulations may bring about proliferation and differentiation of B-lymphocytes.

Formulations of the invention may also bring about an effect oil the acquired immune response. For example, the production of the T helper type 1 (T$_H$1) cytokine IFN-γ may be induced indirectly and the production of the T helper type 2 (T$_H$2) cytokines IL-4, IL-5 and IL-13 may be inhibited upon administration of the formulations.

Formulations of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

The invention thus also provides, for example, a method of heating a viral infection in an animal and a method of treating a neoplastic disease in an animal comprising administering via injection an effective amount of a formulation of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be an amount so as to deliver an IRM compound dose of about 100 ng/kg to about 50 mg/kg, preferably about 1 µg/kg to about 5 mg/kg. An amount of formulation effective to treat a neoplastic condition is an amount that will cause a reduction in tumor size or in the number of tumor foci. Again, the precise amount will vary according to factors known in the art but is expected to be an amount at is given drug concentration to deliver via injection an IRM compound dose of about 100 ng/kg to about 50 mg/kg, for example about 1 µg/kg to about 5 mg/kg.

Particular examples of uses of formulations of the invention delivered via injection include, but are not limited to, treatment of head and neck cancers and breast cancer.

The injectable formulations described herein can include a range of IRM compound concentrations, with lower limits based on minimum therapeutic potency of the IRM compound and upper limits based primarily on solubility of the drug. In general, the concentration of the IRM compound will be from about 0.1 mg/ml to about 10 mg/ml (approximately 0.01% to about 1% by weight). In some embodiments, the IRM compound is present in an amount of from about 0.1 mg/ml to about 6 mg/ml. In some embodiments, the IRM compound is present in an amount of from about 0.5 mg/ml to about 3 mg/ml.

In some embodiments or the methods disclosed herein, the formulation may be administered, for example, from a single dose to multiple doses per week, although in some embodiments the methods of the present invention may be performed by administering the formulation at a frequency outside this range. In some embodiments, the formulation may be administered from about once per month to about five times per week. In some embodiments, the formulation is administered once per week.

The present invention further provides a method of making pharmaceutical formulations comprising ethanol, sesame oil, and an IRM compound of Formula I. In some embodiments, the method of making comprises dissolving the IRM compound in the ethanol to create an ethanol-IRM compound solution. In some embodiments, the IRM compound is fully dissolved in the ethanol, while in some embodiments, small amount of IRM compound will remain undissolved but the majority of IRM compound will be dissolved. The ethanol-IRM compound solution is then mixed with the sesame oil to make the sesame oil-ethanol-IRM compound formulation. In some embodiments, the IRM compound will be fully dissolved in the sesame oil-ethanol-IRM compound formulation, while in some embodiments, small amount of IRM compound will remain undissolved in the sesame oil-ethanol-IRM compound formulation but the majority of IRM compound will be dissolved.

In some embodiments, the method of making comprises mixing the IRM compound with the ethanol and sesame oil simultaneously to make the sesame oil-ethanol-IRM compound formulation. In some embodiments, the IRM compound will be fully dissolved in the sesame oil-ethanol-IRM compound formulation, while in some embodiments, small amount of IRM compound will remain undissolved in the sesame oil-ethanol-IRM compound formulation but the majority of IRM compound will be dissolved.

In some embodiments, the method of making may further include a step of evaporating off a portion of the ethanol from the sesame oil-ethanol-IRM compound formulation. Such method allows faster dissolution of the IRM in the sesame oil-ethanol solution, by allowing use of excess ethanol (ethanol present beyond the solubility limits in sesame oil) during the mixing steps. In some embodiments, after evaporation of a portion of the ethanol, ethanol remains in the final formulation, e.g., 1 wt-% to 9 wt-%.

It will be recognized that any additives described above can be added during any of the above-described mixing steps.

Embodiments of this invention are further illustrated by the following non-limiting examples, but the particular materials and amounts thereof recited in these examples, as well as other conditions and details, should not be construed to unduly limit this invention.

EXAMPLES

Injection Formulation Components

N-(4-{4-amino-2-butyl-1H-imidazo[4,5-c]quinolin-1-yl]oxy}butyl)octadecanamide was prepared according to the synthetic procedure described in Example 1 of U.S. Patent Publication No. 2013/0230578 (Wightman).

Ethanol (200 proof, USP grade) was obtained from Pharmaco-AAPER (Brookfield, Conn.) or Columbus Chemical Industries (Columbus, Wis.). For final formulations containing BHA, a fresh stock sample of deoxygenated ethanol was prepared by passing a gentle flow of dry nitrogen gas through the ethanol (sparging) for about five to ten minutes. The bottle was then immediately capped.

Sesame oil was obtained from Croda Inc. (Edison, N.J.) as the SUPER REFINED® Sesame Oil NF/NP grade product (product code number SR40280) The "NP" designation indicated that the sesame oil did not contain BHT (butylated hydroxytoluene) as an added antioxidant. According to the manufacturer, sesame oil, with the SUPER REFINED® designation was purified using, flash chromatography to remove polar impurities present in the sesame oil. For final formulations containing added BHA, a fresh stock sample of deoxygenated sesame oil was prepared by passing a gentle flow of dry nitrogen gas through the sesame oil (sparging) for about ten to twenty minutes. The bottle was then immediately capped.

Butylated hydroxyanisole, NF grade (BHA) was obtained from Spectrum Chemical Company (New Brunswick, N.J.). The formulations containing BHA were prepared with a BHA concentration of 301) ppm.

Analytical Method

The content of N-(4-{4-amino-2-butyl-1H-imidazo[4,5-c]quinolin-1-yl]oxy}butyl)octadecanamide in the injection formulations was determined using reversed phase high performance liquid chromatography (Agilent 1100 HPLC instrument equipped with a ultraviolet detector set at 321 nm, Agilent Technologies, Santa Clara, Calif.). The analytical column used was a Zorbax Bonus RP column with a 150 mm length, 4.6 mm inner diameter, and 3.5 micron particle site (Agilent Technologies). The column was maintained at 45° C. A gradient elution was conducted with the mobile phase consisting 0.1%) trifluoroacetic acid in water, methanol, and isopropanol. The initial mobile phase consisted of 0.1% trilluoroacetic acid and methanol in a ratio of 85:15. The final mobile phase consisted of 0.1% trifluoroacetie acid, methanol, and isopropanol in a ratio of 5:40:55. The flow rate was 1.0 mL/minute.

Example 1

Injection Formulation: Ethanol (7.5 Weight Percent) in Sesame Oil

N-(4-{4-amino-2-butyl-1H-imidazo[4,5-c]quinolin-1-yl]oxy}butyl)octadecanamide (0.21 g) and ethanol (26.79 g) were added to an amber glass bottle. The bottle was capped and placed in an ultrasonic, bath (Branson model 8510-DTH, Branson Ultrasonics, Danbury, Conn.). The sample was sonicated until all of the N-(4-{4-amino-2-butyl-1H-imidazo[4,5-c]quinolin-1-yl]oxy}butyl)octadecanamide dissolved (about ten minutes). The resulting ethanol solution contained 0.78 weight percent of N-(4-{4-amino-2-butyl-1H-imidazo[4,5-c]quinolin-1-yl]oxy}butyl)octadecanamide bottle. Next, 21.59 g of the ethanol solution containing 0.78 weight percent of N-(4-{4-amino-2-butyl-1H-imidazo[4,5-c]quinolin-1-yl]oxy}butyl)octadecanamide was transferred to an amber glass bottle containing 277.5 g of sesame oil. An additional 1.08 g of ethanol was also added to the bottle. The bottle was capped and then placed on a laboratory roller mixer. The formulation was agitated until it became transparent on visual inspection (agitation for about 15 minutes). In a final step the formulation was passed through a 0.2 micron polyethersulfone (PSA) membrane filter (EMD Millipore, Billerica, Mass.) and 6 mL of the formulation was collected in a clear glass serum vial (Miller Analytical Company, Bristol, Pa.). The headspace in the vial was purged with a stream of dry nitrogen gas and the vial was capped with an aluminum crimp cap containing a gray chlorobutyl-isoprene septum (Miller Analytical Company). The concentration of N-(4-{4-amino-2-butyl-1H-imidazo[4,5-c]quinolin-1]oxy}butyl)octadecanamide in the final formulation was about 0.5 mg/mL.

Example 2

Injection Formulation: Ethanol (7.5 Weight Percent) in Sesame Oil Containing BHA N-(4-{4-amino-butyl-1-1H-imidazo[4,5-c]quinolin-1-yl]oxy}butyl)octadecanamide (0.21 g) and deoxygenated ethanol (26.79 g) were added to an amber glass bottle. The bottle was capped and placed in an ultrasonic bath (Branson model 8510-DTH). The sample was sonicated until all of the N-(4-{4-amino-2-butyl-1H-imidazo[4,5-c]quinolin-1-yl]oxy}butyl)octadecanamide dissolved (about ten minutes). The resulting ethanol solution contained 0.78 weight percent of N-(4-{4-amino-2-butyl-1H-imidazo[4,5-c]quinolin-1-yl]oxy}butyl)octadecanamide bottle. Next, 21.59 g of the ethanol solution containing 0.78 weight percent of N-(4-{4-amino-2-butyl-1H-imidazo[4,5-c]quinolin-1-yl]oxy}butyl)octadecanamide and BHA (90 mg) were transferred to an amber glass bottle containing 277.5 g of deoxygenated sesame oil. An additional 1.08 g of deoxygenated ethanol was also added to the bottle. A gentle stream of dry nitrogen gas was then passed through the formulation for about 10 seconds. The bottle was capped and then placed on a laboratory roller mixer. The formulation was agitated until it became transparent on visual inspection (agitation for about 15 minutes). In a final step the formulation was passed through a 0.2 micron polyethersulfone (PSA) membrane filter (EMD Millipore, Billerica, Mass.) and 6 mL of the formulation was collected in a clear glass serum vial (Miller Analytical Company, Bristol, Pa.). The headspace in the vial was purged with a stream of dry nitrogen gas and the vial was capped with an aluminum crimp cap containing a gray chlorobutyl-isoprene septum (Miller Analytical Company). The concentration of N-(4-{4-amino-2-butyl-1H-imidazo[4,5-c]quinolin-1-yl]oxy}butyl)octadecanamide in the final formulation was about 0.5 mg/mL.

Example 3

Injection Formulation: Ethanol (5 Weight Percent) in Sesame Oil

N-(4-{4-amino-2-butyl-1H-imidazo[4,5-c]quinolin-1-yl]oxy}butyl)octadecanamide (0.30 g) and ethanol (15.0 g) were added to an amber glass bottle. The bottle was capped and placed in an ultrasonic bath (Branson model 8510-DTH). The sample was sonicated until all of the N-(4-{4-amino-2-butyl-1H-imidazo[4,5-c]quinolin-1-yl]oxy}butyl)octadecanamide dissolved (about ten minutes). The resulting ethanol solution contained 2.0 weight percent of N-(4-{4-amino-2-butyl-1H-imidazo[4,5-c]quinolin-1-yl]oxy}butyl)octadecanamide bottle. Next, 0.29 g of the ethanol solution containing 2.0 weight percent of N-(4-{4-amino-2-butyl-1H-imidazo[4,5-c]quinolin-1-yl]oxy}-butyl)octadecanamide was transferred to an amber glass bottle containing 10.5 g of sesame oil. An additional 0.23 g of ethanol was also added to the bottle. The bottle was capped and then placed on a laboratory roller mixer. The formulation was agitated until it became transparent on visual inspection (agitation for about 15 minutes). In a final step the formulation was passed through a 0.2 micron polyethersulfone (PSA) membrane filter (EMD Millipore, Billerica, Mass.) and 6 mL of the formulation was collected in a clear glass serum vial (Miller Analytical Company, Bristol, Pa.). The headspace in the vial was purged with a stream of dry nitrogen gas and the vial was capped with an aluminum crimp cap containing a gray chlorobutyl-isoprene septum (Miller Analytical Company). The concentration of N-(4-{4-amino-2-butyl-1H-imidazo[4,5-c]quinolin-1-yl]oxy}butyl)octadecanamide in the final formulation was about 0.5 mg/mL.

Example 4

Injection Formulation: Ethanol (9 Weight Percent) in Sesame Oil

N-(4-{4-amino-2-butyl-1H-imidazo[4,5-c]quinolin-1-yl]oxy}butyl)octadecanamide (0.30 g) and ethanol (15.0 g) were added to an amber glass bottle. The bottle was capped and placed in an ultrasonic bath (Branson model 8510-DTH). The sample was sonicated until all of the N-(4-{4-amino-2-butyl-1-H-imidazo[4,5-c]quinolin-1-yl]oxy}butyl)octadecanamide dissolved (about ten minutes). The resulting ethanol solution contained 2.0 weight percent of N-(4-{4-amino-2-butyl-1H-imidazol4,5-c]quinolin-1-yl]oxy}butyl)octadecanamide bottle. Next, 3.0 g of the ethanol solution containing 2.0 weight percent of N-(4-{4-amino-2-butyl-1H-imidazo[4,5-c]quinolin-1-yl]oxy}butyl)octadecanamide was transferred to an amber glass bottle containing 54.5 g of sesame oil. An additional 2.4 g of ethanol was also added to the bottle. The bottle was capped and then placed on a laboratory roller mixer. The formulation was agitated until it became transparent on visual inspection (agitation for about 15 minutes). In a final step the formulation was passed through a 0.2 micron polyethersulfone (PSA) membrane filter (EMD Millipore, Billerica, Mass.) and 6 mL of the formulation was collected in a clear glass serum vial (Miller Analytical Company, Bristol, Pa.). The headspace in the vial was purged with a stream of dry nitrogen gas and the vial was capped with an aluminum crimp cap containing a gray chlorobutyl-isoprene septum (Miller Analytical Company). The concentration of N-(4-{4-amino-2-butyl-1H-imidazo[4,5-c]quinolin-1-yl]oxy}butyl)octadecanamide in the final formulation was about 1 mg/mL.

Example 5

Injection Formulation: Ethanol (8.5 Weight Percent) in Sesame Oil

N-(4-{4-amino-2-butyl-1H-imidazo[4,5-c]quinolin-1-yl]oxy}butyl)octadecanamide (1.22 g) and ethanol (60.0 g)

were added to an amber glass bottle. The bottle was capped and placed in an ultrasonic bath (Branson model 8510-DTH). The sample was sonicated until all of the N-(4-{4-amino-2-butyl-1H-imidazo[4,5-c]quinolin-1-yl]oxy}butyl)octadecanamide dissolved (about thirty minutes). The resulting ethanol solution contained 2.0 weight percent of N-(4-{4-amino-2-butyl-1H-imidazo[4,5-c]quinolin-1-yl]oxy}butyl)octadecanamide bottle. Next, 9.0 g of the ethanol solution containing 2.0 weight percent of N-(4-{4-amino-2-butyl-1H-imidazo[4,5-c]quinolin-1-yl]oxy}butyl)octadecanamide was transferred to an amber glass bottle containing (60.0 g of sesame oil. The bottle was capped and then placed on a laboratory roller mixer. The formulation was agitated until it became transparent on visual inspection (agitation for about 15 minutes). A stream of dry nitrogen gas was passed over the stirred formulation to evaporate 3.4 g of ethanol. In a final step the formulation was passed through a 0.2 micron polyethersulfone (PSA) membrane filter (EMD Millipore, Billerica, Mass.) and 6 mL of the formulation was collected in a clear glass serum vial (Miller Analytical Company, Bristol, Pa.), The headspace the vial was purged with a stream of dry nitrogen gas and the vial was capped with an aluminum crimp cap containing a gray chlorobutyl-isoprene septum (Miller Analytical Company). The concentration of N-(4-{4-amino-2-butyl-1H-imidazo[4,5-c]quinolin-1-yl]oxy}butyl)octadecanamide in the final formulation was about 3 mg/mL.

Example 6

Injection Formulation: Ethanol (9 Weight Percent) in Sesame Oil

N-(4-{4-amino-2-butyl-1H-imidazo[4,5-c]quinolin-1-yl]oxy}butyl)octadecanamide (1.22 g) and ethanol (60.0 g) were added to an amber glass bottle. The bottle was capped and placed in an ultrasonic bath (Branson model 8510-DTH). The sample was sonicated until all of the N-(4-{4-amino-2-butyl-1H-imidazo[4,5-c]quinolin-1-yl]oxy}butyl)octadecanamide dissolved (about thirty minutes). The resulting ethanol solution contained 2.0 weight percent of N-(4-{4-amino-2-butyl-1H-imidazo[4,5-c]quinolin-1-yl]oxy}butyl)octadecanamide bottle. Next, 25.0 g of the ethanol solution containing 2.0 weight percent of N-(4-{4-amino-2-butyl-1H-imidazo[4,5-c]quinolin-1-yl]oxy}butyl)octadecanamide was transferred to an amber glass bottle containing 90.5 g of sesame oil. The bottle was capped and then placed on a laboratory roller mixer. The formulation was agitated until it became transparent on visual inspection (agitation for about 15 minutes). A stream of dry nitrogen gas was passed over the stirred formulation to evaporate 15.5 g of ethanol. In a final step the formulation was passed through a 0.2 micron polyethersulfone (PSA) membrane filter (EMD Millipore, Billerica, Mass.) and 6 mL of the formulation was collected in a clear glass serum vial (Miller Analytical Company, Bristol, Pa.). The headspace in the vial was purged with a stream of dry nitrogen gas and the vial was capped with an aluminum crimp cap containing a gray chlorobutyl-isoprene septum (Miller Analytical Company). The concentration of N-(4-{4-amino-2-butyl-1H-imidazo[4,5-c]quinolin-1-yl]oxy}butyl)octadecanamide in the final formulation was about 5 mg/mL.

Example 7

Injection Formulation: Ethanol (6.5 Weight Percent) in Sesame Oil

N-(4-{4-amino-2-butyl-1H-imidazo[4,5-c]quinolin-1-yl]oxy}butyl)octadecanamide (0.30 g) and ethanol (15.3 g) were added to an amber glass bottle. The bottle was capped and placed in an ultrasonic bath (Branson model 8510-DTH). The sample was sonicated until all of the N-(4-{4-amino-2-butyl-1H-imidazo[4,5-c]quinolin-1-yl]oxy}butyl)octadecanamide dissolved (about ten minutes). The resulting ethanol solution contained 1.9 weight percent of N-(4-{4-amino-2-butyl-1-imidazo[4,5-c]quinolin-1-yl]oxy}butyl)octadecanamide bottle. Next, 0.18 g of the ethanol solution containing 1.9 weight percent of N-(4-{4-amino-2-butyl-1H-imidazo[4,5-c]quinolin-1-yl]oxy}butyl)octadecanamide was transferred to an amber glass bottle containing 31.7 g of sesame oil. An additional 2.0 g of ethanol was also added to the bottle. The bottle was capped and then placed on a laboratory roller mixer. The formulation was agitated until it became transparent on visual inspection (agitation for about 15 minutes). In a final step the formulation was passed through a 0.2 micron polyethersulfone (PSA) membrane filter (EMD Millipore, Billerica, Mass.) and 6 mL of the formulation was collected in a clear glass serum vial (Miller Analytical Company, Bristol, Pa.). The headspace in the vial was purged with a stream of dry nitrogen gas and the vial was capped with an aluminum crimp cap containing a gray chlorobutyl-isoprene septum (Miller Analytical Company). The concentration of N-(4-{4-amino-2-butyl-1H-imidazo[4,5-c]quinolin-1-yl]oxy}butyl)octadecanamide in the final formulation was about 0.1 mg/mL.

Example 8

Injection Formulation: Ethanol (7.2 Weight Percent) in Sesame Oil

A solution of ethanol (7.2 weight percent) in sesame oil was prepared by adding 3.9 g of ethanol and 50.0 g of sesame oil to an amber bottle followed by gentle stirring. N-(4-{4-amino-2-butyl-1H-imidazo[4,5-c]quinolin-1-yl]oxy}butyl)octadecanamide (53.9 mg) was then added to the ethanol/sesame oil solution. The bottle was capped and placed in an ultrasonic bath (Branson model 8510-DTH). The sample was sonicated for 30 minutes and then further shaken using a shaker table (Erbach Corporation, Ann Arbor, Mich.) until all of the N-(4-{4-amino-2-butyl-1H-imidazo[4,5-c]quinolin-1-yl]oxy}-butyl)octadecanamide was dissolved (about 20 hours). The resulting solution was passed through a 0.2 micron polyethersulfone (PSA) membrane filter (EMD Millipore, Billerica, Mass.) and collected in a glass bottle. The headspace in the bottle was purged with a stream of dry nitrogen gas and the bottle was capped. The concentration of N-(4-{4-amino-2-butyl-1H-imidazo[4,5-c]quinolin-1-yl]oxy}butyl)octadecanamide in the final formulation was about 1 mg/g.

Example 9

Additional Injection Formulations

A variety of formulations with differing levels of ethanol concentration (weight percent of ethanol in the formulation), N-(4-{4-amino-2-butyl-1H-imidazo[4,5-c]quinolin-1-yl]oxy}butyl)octadecanamide concentration (mg/mL of formulation), and BHA concentration (ppm) were prepared using the general procedures of Examples 1-7. For Formulations 9-H thru 9-J deoxygenated ethanol and sesame oil were used. The formulations are reported in Table 1.

Formulations were prepared in which the ethanol content of the formulation was reduced by including an ethanol evaporation step immediately prior to the final filtration step. The evaporation of the ethanol in the formulation was accomplished by passing a stream of dry nitrogen gas over the stirred formulation.

TABLE 1

| Formulation Designation | Concentration of Ethanol in the Injection Formulation (weight percent) | Concentration of N-(4-{4-amino-2-butyl-1H-imidazo[4,5-c]quinolin-1-yl]oxy}butyl)octadecanamide in the Injection Formulation (mg/mL) | BHA Concentration (ppm) |
|---|---|---|---|
| 9-A | 5 | 0.1 | 0 |
| 9-B | 5 | 1 | 0 |
| 9-C | 6 | 0.1 | 0 |
| 9-D | 6 | 0.3 | 0 |
| 9-E | 6 | 1 | 0 |
| 9-F | 7 | 0.4 | 0 |
| 9-G | 7 | 0.5 | 0 |
| 9-H | 7 | 2.5 | 300 |
| 9-I | 7.5 | 1.5 | 300 |
| 9-J | 7.5 | 2.5 | 300 |
| 9-K | 9 | 3 | 0 |
| 9-L | 9 | 5 | 0 |

Example 10

Intratumoral (IT) Injection

All procedures were conducted in accordance with approved Institutional Animal Care and Use Committee (IACUC) protocols. The animals were housed in as facility that was accredited by the Association for Assessment and Accreditation of Laboratory Animal Care (AAALAC, Frederick, Md.) C57BL6J-Tyr Albino mice, female. 15-20 grams were obtained from Jackson Labs, Bar Harbor, Me. The syngeneic B16.OVA melanoma cell line was obtained from Dr. Wynette Dietz, University of Minnesota. The cell line was characterized at 3M and determined to express OVA.

Prior to establishing tumor-bearing mice, the animals were anesthetized with 1% isoflurane in an airtight box and then maintained under anesthesia by administration of 1% isoflurane via a face mask. Each mouse was given a unique descriptor (unique tattooed number on the tail). The right flank was shaved and $5\times10^5$ B16.OVA melanoma cells, in 0.1 mL DPBS were implanted subcutaneously.

Seven days after tumor implantation the mice were randomized into 3 groups (Groups A-C) of 20 mice per group. At this point the average tumor size in the mice was approximately 20 mm². Animals that were outliers based on tumor sire were identified and excluded from the study based on the ROUT statistical method developed by Graph-Pad Software (La Jolla, Calif.). The Group A animals received a 0.05 mL intratumoral injection of the form elation of Example 3. The Group B animals received a 0.05 mL injection of the Formulation of Example 3 administered subcutaneously (SC) into the flank region opposite from the implanted tumor (i.e. left flank). The Group C animals received a 0.05 ml, intratumoral injection of a Vehicle Control Formulation. The Vehicle Control Formulation was the same as the Formulation of Example 3 with the exception that N-(4-{4-amino-2-butyl-1H-imidazo[4,5-c]quinolin-1-yl]oxy}butyl)octadecanamide was not included in the formulation. All of the formulations for Groups A-C were administered using a 0.5 mL syringe with a 26 gauge needle. All three groups were injected with the corresponding formulation at 7 days and 14 days after the tumor implantation. For Groups A and C the intratumoral injection was administered in the center of the tumor. Prior to injection, the animals were anesthetized with 1% isoflurane via a face mask. For each animal, the tumor size was measured with a calibrated digital caliper. All tumors were palpable and visible. If the tumor size was measured to be 200 mm² or greater, the animal was euthanized. The animals were monitored for 90 days post tumor implantation. For each animal, the tumor size data is reported in Tables 2A-C, and the percent survival data is reported in Table 3. The median survival in days was 34 days for Group A, 22 days for group B, and 21.5 days for Group C. The animal survival data was analyzed using Prism 5.04 software (GraphPad Software). Kaplan-Meier survival curves were compared by the log-rank (Mantel-Cox) test followed by painwise comparison using the Gehan-Breslow-Wilcoxon test. The survival advantage of the Group A animals versus group B and C animals was determined to be statistically significant (p value<0.0001).

Example 11

A variety of formulations with fixed levels of ethanol concentration (at 7.5 wt-% of ethanol in the formulation), differing levels of N-(4-{[4-amino-2-butyl-1H-imidazo[4,5-c]quinolin-1-yl]oxy}butyl)octadecanamide concentrations ranging from 0.1 mg/mL to 2.5 mg/mL, and BHA concentrations (300 ppm) are prepared using the general procedures of Examples 1-7. For Formulations 11-A thru 11-E deoxygenated ethanol and sesame oil are used. The formulations are reported in Table 4.

Formulations are prepared in which the ethanol content of the formulation is reduced by including an ethanol evaporation step immediately prior to the final filtration step. The evaporation of the ethanol in the formulation is accomplished by passing a stream of dry nitrogen gas over the stirred formulation.

TABLE 4

| Formulation Designation | Concentration of Ethanol in the Injection Formulation (weight percent) | Concentration of N-(4-{[4-amino-2-butyl-1H-imidazo[4,5-c]quinolin-1-yl]oxy}butyl)octadecanamide in the Injection Formulation (mg/mL) | BHA Concentration (ppm) |
|---|---|---|---|
| 11-A | 7.5 | 0.15 | 300 |
| 11-B | 7.5 | 0.3 | 300 |
| 11-C | 7.5 | 0.6 | 300 |
| 11-D | 7.5 | 1.2 | 300 |
| 11-E | 7.5 | 2.4 | 300 |

TABLE 2A

Group A (IT Injection of the Example 3 Formulation): Tumor Size

| Days Post Tumor Implantation | A1 | A2 | A3 | A4 | A5 | A6 | A7 | A8 | A9 | A10 |
|---|---|---|---|---|---|---|---|---|---|---|
| 8 | 21 | 15 | 20 | 24 | 12 | 18 | 34 | 17 | 25 | 14 |
| 15 | 13 | 31 | 36 | 42 | 25 | 38 | 187 | 46 | 65 | 18 |
| 16 | NM | NM | NM | NM | NM | NM | 226* | NM | NM | NM |
| 19 | 22 | 32 | 54 | 73 | 65 | 48 |  | 68 | 104 | 33 |
| 21 | NM | NM | NM | NM | NM | NM |  | NM | NM | NM |
| 22 | NM | 20 | 45 | 108 | 43 | 58 |  | 104 | 132 | 40 |
| 23 | NM | NM | NM | NM | NM | NM |  | NM | NM | NM |
| 26 | 37 | 36 | 74 | 137 | 185 | 75 |  | 131 | 161 | 90 |
| 27 | NM | NM | NM | NM | NM | NM |  | NM | NM | NM |
| 28 | NM | NM | NM | NM | 180 | NM |  | NM | 245* | NM |
| 30 | 44 | 42 | 54 | 197* | 309* | 112 |  | 240* |  | 35 |
| 34 | 42 | 43 | 66 |  |  | 198* |  |  |  | 43 |
| 36 | 50 | 39 | 61 |  |  |  |  |  |  | 29 |
| 40 | 75 | 35 | 67 |  |  |  |  |  |  | 41 |
| 47 | 278* | 46 | 70 |  |  |  |  |  |  | 41 |
| 51 |  | 38 | NM |  |  |  |  |  |  | NM |
| 54 |  | NM | NM |  |  |  |  |  |  | NM |
| 55 |  | 38 | 73 |  |  |  |  |  |  | 41 |
| 62 |  | 44 | 154 |  |  |  |  |  |  | 28 |
| 64 |  | 45 | 271* |  |  |  |  |  |  | 42 |
| 75 |  | 163* |  |  |  |  |  |  |  | 46 |
| 90 |  |  |  |  |  |  |  |  |  | 50 |

| Days Post Tumor Implantation | A11 | A12 | A13 | A14 | A15 | A16 | A17 | A18 | A19 | A20 |
|---|---|---|---|---|---|---|---|---|---|---|
| 8 | 12 | 16 | 18 | 24 | 26 | 22 | 26 | 33 | 19 | 11 |
| 15 | 67 | 23 | 28 | 58 | 63 | 17 | 16 | 53 | 39 | 36 |
| 16 | NM | NM | NM | NM | NM | NM | NM | NM | NM | NM |
| 19 | 70 | 51 | 47 | 89 | 87 | 71 | 30 | 69 | 47 | 36 |
| 21 | NM | NM | NM | NM | NM | NM | NM | NM | NM | NM |
| 22 | 97 | 44 | 65 | 317* | 99 | 49 | 36 | 105 | 61 | 45 |
| 23 | NM | NM | NM |  | NM | NM | NM | NM | NM | NM |
| 26 | 113 | 35 | 67 |  | 90 | 88 | 59 | 149 | 97 | 58 |
| 27 | NM | NM | NM |  | NM | NM | NM | NM | NM | NM |
| 28 | NM | NM | NM |  | NM | 107 | NM | 152 | NM | NM |
| 30 | 144 | 81 | 61 |  | 92 | 81 | 48 | 217* | 171 | 40 |
| 34 | 212* | 57 | 125 |  | 139 | 244* | 77 |  | 350* | 79 |
| 36 |  | 30 | 176 |  | 225* |  | 63 |  |  | 51 |
| 40 |  | 49 | 284* |  |  |  | 156 |  |  | 43 |
| 47 |  | 97 |  |  |  |  | 72 |  |  | 124 |
| 51 |  | 160 |  |  |  |  | 158 |  |  | 222* |
| 54 |  | 235* |  |  |  |  | 193 |  |  |  |
| 55 |  |  |  |  |  |  | 241* |  |  |  |
| 62 |  |  |  |  |  |  |  |  |  |  |
| 64 |  |  |  |  |  |  |  |  |  |  |
| 75 |  |  |  |  |  |  |  |  |  |  |
| 90 |  |  |  |  |  |  |  |  |  |  |

The * designation after a value indicates that the animal was euthanized post measurement per the experimental protocol (Example 10);
NM indicates not measured.

TABLE 2B

Group B (SC Injection of the Example 3 Formulation into the Flank Region Opposite from the Tumor): Tumor Size

| Days Post Tumor Implantation | B1 | B2 | B3 | B4 | B5 | B6 | B7 | B8 | B9 | B10 |
|---|---|---|---|---|---|---|---|---|---|---|
| 8 | 22 | 41 | 26 | 13 | 24 | 14 | 26 | 26 | 24 | 4 |
| 15 | 99 | 51 | 44 | 157 | 53 | 68 | 112 | 132 | 127 | 12 |
| 16 | 141 | NM | 137 | 250* | NM | NM | NM | 135 | 140 | NM |
| 19 | 250* | 89 | 200* |  | 84 | 112 | 135 | 228* | 227* | 18 |
| 21 |  | NM |  |  | NM | NM | NM |  |  | NM |
| 22 |  | 146 |  |  | 149 | 261* | 223* |  |  | 19 |
| 23 |  | 156 |  |  | 182 |  |  |  |  | NM |

TABLE 2B-continued

Group B (SC Injection of the Example 3 Formulation into the Flank Region Opposite from the Tumor): Tumor Size

| | | | |
|---|---|---|---|
| 26 | 205* | 173 | 28 |
| 27 | | NM | NM |
| 28 | | 212* | NM |
| 30 | | | 49 |
| 34 | | | 142 |
| 36 | | | 215* |
| 40 | | | |
| 47 | | | |
| 51 | | | |
| 54 | | | |
| 55 | | | |
| 62 | | | |
| 64 | | | |
| 75 | | | |
| 90 | | | |

| Days Post Tumor Implantation | Tumor Size (mm$^2$) for Each Animal in Group B | | | | | | | | | |
|---|---|---|---|---|---|---|---|---|---|---|
| | B11 | B12 | B13 | B14 | B15 | B16 | B17 | B18 | B19 | B20 |
| 8 | 20 | 26 | 24 | 30 | 24 | 5 | 26 | 21 | 0 | 22 |
| 15 | 120 | 74 | 91 | 68 | 19 | 34 | 52 | 52 | 17 | 24 |
| 16 | 135 | NM | NM | NM | NM | NM | NM | NM | NM | NM |
| 19 | 381* | 165 | 157 | 106 | 18 | 105 | 158 | 84 | 25 | 51 |
| 21 | | 265* | 203* | NM | NM | 163 | 202* | NM | NM | NM |
| 22 | | | | 186* | 52 | 238* | | 104 | 53 | 77 |
| 23 | | | | | NM | | | NM | NM | NM |
| 26 | | | | | 114 | | | 130 | 86 | 123 |
| 27 | | | | | NM | | | NM | NM | 205* |
| 28 | | | | | NM | | | NM | NM | |
| 30 | | | | | 240* | | | 223* | 276* | |
| 34 | | | | | | | | | | |
| 36 | | | | | | | | | | |
| 40 | | | | | | | | | | |
| 47 | | | | | | | | | | |
| 51 | | | | | | | | | | |
| 54 | | | | | | | | | | |
| 55 | | | | | | | | | | |
| 62 | | | | | | | | | | |
| 64 | | | | | | | | | | |
| 75 | | | | | | | | | | |
| 90 | | | | | | | | | | |

The * designation after a value indicates that the animal was euthanized post measurement per the experimental protocol (Example 10);
NM indicates not measured.

TABLE 2C

Group C (IT Injection of the Vehicle Control Formulation): Tumor Size

| Days Post Tumor Implantation | Tumor Size (mm$^2$) for Each Animal in Group C | | | | | | | | | |
|---|---|---|---|---|---|---|---|---|---|---|
| | C1 | C2 | C3 | C4 | C5 | C6 | C7 | C8 | C9 | C10 |
| 8 | 11 | 18 | 17 | 42 | 10 | 24 | 16 | 12 | 40 | 31 |
| 15 | 54 | 13 | 51 | 179 | 46 | 180 | 50 | 94 | 90 | 132 |
| 16 | NM | NM | NM | 263* | NM | 248* | NM | NM | NM | 184* |
| 19 | 165 | 27 | 98 | | 103 | | 107 | 248* | 120 | |
| 21 | 144 | NM | NM | | NM | | 144 | | NM | |
| 22 | 130 | 26 | 133 | | 168 | | 135 | | 183 | |
| 23 | 178 | NM | NM | | 134 | | NM | | 210* | |
| 26 | 223* | 35 | 226* | | 141 | | 166 | | | |
| 27 | | NM | | | NM | | NM | | | |
| 28 | | NM | | | 183 | | 216* | | | |
| 30 | | 46 | | | 258* | | | | | |
| 34 | | 104 | | | | | | | | |
| 36 | | 132 | | | | | | | | |
| 40 | | 150 | | | | | | | | |
| 43 | | 216* | | | | | | | | |
| 47 | | | | | | | | | | |
| 51 | | | | | | | | | | |
| 54 | | | | | | | | | | |
| 55 | | | | | | | | | | |

TABLE 2C-continued

| Group C (IT Injection of the Vehicle Control Formulation): Tumor Size | | | | | | | | | |
|---|---|---|---|---|---|---|---|---|---|
| 62 | | | | | | | | | |
| 64 | | | | | | | | | |
| 75 | | | | | | | | | |
| 90 | | | | | | | | | |

| Days Post Tumor Implantation | Tumor Size (mm²) for Each Animal in Group C | | | | | | | | | |
|---|---|---|---|---|---|---|---|---|---|---|
| | C11 | C12 | C13 | C14 | C15 | C16 | C17 | C18 | C19 | C20 |
| 8 | 16 | 42 | 12 | 11 | 23 | 21 | 18 | 27 | 25 | 14 |
| 15 | 82 | 60 | 90 | 66 | 118 | 104 | 35 | 73 | 78 | 68 |
| 16 | NM | NM | NM | NM | 203* | 172 | NM | NM | NM | NM |
| 19 | 144 | 100 | 243* | 153 | | 317* | 57 | 205* | 220* | 83 |
| 21 | 189 | NM | | 259* | | | NM | | | 83 |
| 22 | 240* | 158 | | | | | 83 | | | 205* |
| 23 | | 192* | | | | | NM | | | |
| 26 | | | | | | | 91 | | | |
| 27 | | | | | | | NM | | | |
| 28 | | | | | | | NM | | | |
| 30 | | | | | | | 208* | | | |
| 34 | | | | | | | | | | |
| 36 | | | | | | | | | | |
| 40 | | | | | | | | | | |
| 43 | | | | | | | | | | |
| 47 | | | | | | | | | | |
| 51 | | | | | | | | | | |
| 54 | | | | | | | | | | |
| 55 | | | | | | | | | | |
| 62 | | | | | | | | | | |
| 64 | | | | | | | | | | |
| 75 | | | | | | | | | | |
| 90 | | | | | | | | | | |

The * designation after a value indicates that the animal was euthanized post measurement per the experimental protocol (Example 10);
NM indicates not measured.

TABLE 3

| | Proportion of Surviving Mice | | |
|---|---|---|---|
| Days Post Tumor Implantation | Group A (IT administration of Example 3 Formulation) | Group B (SC administration of Example 3 Formulation) | Group C (IT administration of Vehicle Control Formulation) |
| 0 | 100 | 100 | 100 |
| 16 | 95 | 95 | 80 |
| 19 | 95 | 70 | 55 |
| 21 | 95 | 35 | 50 |
| 22 | 90 | 35 | 40 |
| 23 | 90 | 35 | 30 |
| 26 | 90 | 30 | 20 |
| 27 | 90 | 25 | 20 |
| 28 | 85 | 20 | 15 |
| 30 | 65 | 5 | 5 |
| 34 | 45 | 5 | 5 |
| 36 | 40 | 0 | 5 |
| 40 | 35 | 0 | 5 |
| 43 | 35 | 0 | 0 |
| 47 | 30 | 0 | 0 |
| 51 | 25 | 0 | 0 |
| 54 | 20 | 0 | 0 |
| 55 | 15 | 0 | 0 |
| 64 | 10 | 0 | 0 |
| 75 | 5 | 0 | 0 |
| 90 | 5 | 0 | 0 |

What is claimed is:

1. An intratumoral injectable pharmaceutical formulation, comprising:
   sesame oil having a hydroxyl value less than or equal to 2, an acid value less than or equal to 0.1, and a peroxide value less than or equal to 1;
   ethanol; and
   an immune response modifier compound, wherein the immune response modifier compound is N-(4-{[4-amino-2-butyl-1H-imidazo[4,5-c]quinolin-1-yl]oxy}butyl)octadecanamide, or a pharmaceutically acceptable salt thereof,
   wherein the ethanol is present in a concentration of from about 1 wt-% to about 9 wt-%.

2. The formulation according to claim 1, wherein the ethanol is present in a concentration of from about 3 wt-% to about 8 wt-%.

3. The formulation according to claim 1, wherein the ethanol is present in a concentration of from about 6.5 wt-% to about 7.5 wt-%.

4. The formulation according to claim 1, wherein the immune response modifier compound is present in a concentration of from about 0.1 mg/mL to about 10 mg/mL.

5. The formulation according to claim 1, wherein the total nitrogen content of the sesame oil is less than or equal to 1 ppm.

6. The formulation according to claim 1, wherein the sesame oil contains no more than 0.05 wt-% of sesamin and no more than 0.05 wt-% of sesamolin.

7. The formulation of claim 1, wherein the formulation comprises:
   7.5 wt-% ethanol;
   300 ppm butylated hydroxyanisole (BHA); and
   from 0.1 mg/mL to about 2.5 mg/mL N-(4-{[4-amino-2-butyl-1H-imidazo[4,5-c]quinolin-1-yl]oxy}butyl)octadecanamide.

8. An intratumoral injectable pharmaceutical formulation, comprising sesame oil having a hydroxyl value less than or equal to 2, an acid value less than or equal to 0.1, and a peroxide value less than or equal to 1, and ethanol; and an immune response modifier compound, wherein the immune response modifier compound is N-(4-{[4-amino-2-butyl-1H-imidazo[4,5-c]quinolin-1-yl]oxy}butyl)octadecanamide or a pharmaceutically acceptable salt thereof, wherein the composition is not aqueous.

9. The formulation of claim 1, wherein the sesame oil has a total nitrogen content of less than or equal to 1 ppm.

10. The formulation of claim 1, wherein the sesame oil contains no more than 0.05 wt-% of sesamin.

11. The formulation of claim 1, wherein the sesame oil contains no more than 0.05 wt-% of sesamolin.

* * * * *